US010351503B2

(12) United States Patent
Smith et al.

(10) Patent No.: US 10,351,503 B2
(45) Date of Patent: Jul. 16, 2019

(54) PROCESS FOR PRODUCING ALDEHYDES

(71) Applicant: Dow Technology Investments LLC, Midland, MI (US)

(72) Inventors: Gerald L. Smith, Dickinson, TX (US); Kathleen Simpson, Gandeeville, WV (US)

(73) Assignee: Dow Technology Investments LLC, Midland, MI (US)

( * ) Notice: Subject to any disclaimer, the term of this patent is extended or adjusted under 35 U.S.C. 154(b) by 0 days.

(21) Appl. No.: 15/768,397

(22) PCT Filed: Oct. 27, 2016

(86) PCT No.: PCT/US2016/058984
§ 371 (c)(1),
(2) Date: Apr. 13, 2018

(87) PCT Pub. No.: WO2017/083106
PCT Pub. Date: May 18, 2017

(65) Prior Publication Data
US 2018/0305285 A1    Oct. 25, 2018

Related U.S. Application Data

(60) Provisional application No. 62/253,353, filed on Nov. 10, 2015.

(51) Int. Cl.
C07C 45/50 (2006.01)
B01L 3/14 (2006.01)
B01J 31/02 (2006.01)
B01J 31/40 (2006.01)
C07C 47/02 (2006.01)

(52) U.S. Cl.
CPC .......... *C07C 45/50* (2013.01); *B01J 31/0267* (2013.01); *B01J 31/4046* (2013.01); *B01L 3/14* (2013.01); *C07C 47/02* (2013.01); *B01J 2531/822* (2013.01); *Y02P 20/582* (2015.11)

(58) Field of Classification Search
CPC .................................................... C07C 45/50
See application file for complete search history.

(56) References Cited

U.S. PATENT DOCUMENTS

| | | | |
|---|---|---|---|
| 3,415,906 A | 12/1968 | Shepard et al. | |
| 3,527,809 A * | 9/1970 | Smith | C07C 45/49 502/162 |
| 4,148,830 A | 4/1979 | Pruett et al. | |
| 4,247,486 A | 1/1981 | Brewester et al. | |
| 4,329,507 A | 5/1982 | Takeda et al. | |
| 4,518,809 A | 5/1985 | Forster et al. | |
| 4,528,403 A | 7/1985 | Tano et al. | |
| 4,567,302 A | 1/1986 | Sivaramakrishnan | |
| 4,567,306 A | 1/1986 | Dennis et al. | |
| 4,599,206 A | 7/1986 | Billig et al. | |
| 4,668,651 A | 5/1987 | Billig et al. | |
| 4,717,775 A | 1/1988 | Billig et al. | |
| 4,774,361 A | 9/1988 | Maher et al. | |
| 4,792,636 A | 12/1988 | Hensman et al. | |
| 4,835,299 A | 5/1989 | Maher et al. | |
| 5,053,551 A * | 10/1991 | Harrison | C07C 45/49 568/451 |
| 5,093,535 A | 3/1992 | Harrison et al. | |
| 5,102,505 A | 4/1992 | Sorensen | |
| 5,110,990 A * | 5/1992 | Blessing | C07C 45/49 568/454 |
| 5,288,918 A | 2/1994 | Maher et al. | |
| 5,360,938 A | 11/1994 | Babin et al. | |
| 5,410,091 A | 4/1995 | Nall | |
| 5,491,266 A | 2/1996 | Babin et al. | |
| 5,728,893 A | 3/1998 | Becker et al. | |
| 5,741,942 A | 4/1998 | Bryant et al. | |
| 5,741,944 A | 4/1998 | Bryant et al. | |
| 6,090,987 A | 7/2000 | Billig et al. | |
| 7,863,487 B2 | 1/2011 | Eisenschmid et al. | |
| 2013/0316893 A1 | 11/2013 | Kim et al. | |

FOREIGN PATENT DOCUMENTS

| | | |
|---|---|---|
| GB | 1338225 A | 11/1973 |
| WO | 2006/115644 A2 | 11/2006 |
| WO | 2010/003073 A1 | 1/2010 |
| WO | 2014/149915 A1 | 9/2014 |
| WO | 2016/089602 A1 | 6/2016 |

OTHER PUBLICATIONS

Brown, Journal of the Chemical Society, 1970, pp. 2753-2764.
PCT/US2016/058984, International Search Report and Written Opinion dated Dec. 19, 2016.
PCT/US2016/058984, International Preliminary Report on Patentability dated May 24, 2018.

* cited by examiner

*Primary Examiner* — Sikarl A Witherspoon

(57) ABSTRACT

The present invention relates generally to processes for producing aldehydes wherein an olefinic compound, carbon monoxide, and hydrogen are reacted in the presence of a solubilized rhodium-phosphorous complex. In one embodiment, the process comprises (a) receiving a vaporized aldehyde product stream downstream from a hydroformylation reactor, the vaporized aldehyde product stream comprising aldehydes, phosphorous ligand, and aldehyde condensation by-products; (b) contacting the vaporized aldehyde product stream with a partial condenser so as to condense the phosphorous ligand and the by-products, wherein up to 10 weight percent of the vaporized stream is condensed; (c) removing the condensed phosphorous ligand and the condensed by-products from the liquid condensation stream using a refining column; and (d) further processing the vaporized aldehydes from the separate refining column.

12 Claims, 1 Drawing Sheet

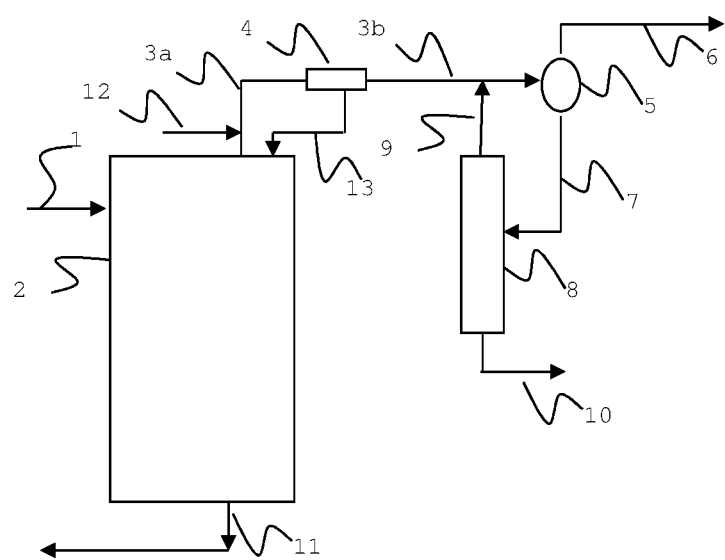

PROCESS FOR PRODUCING ALDEHYDES

FIELD

The present invention relates to the preparation of aldehydes by a hydroformylation process in which an alpha-olefin is hydroformylated with carbon monoxide and hydrogen in the presence of an organophosphine-modified rhodium catalyst, preferably a triarylphosphine. In some embodiments, a process of the present invention is a continuous one for producing aldehydes by the hydroformylation of alpha-olefins containing two to twenty carbon atoms.

INTRODUCTION

U.S. Pat. No. 3,527,809 ("the '809 patent") discloses a significant development in the hydroformylation of alpha-olefins to produce aldehydes at high yields, at low temperatures and pressures, with excellent catalyst stability, and which when the alpha-olefin contains 3 or more carbon atoms, produces aldehyde mixtures containing a high normal to iso-(or branched-chain) isomer ratio. The process employs certain rhodium complex compounds to effectively catalyze, under a defined set of variables in the presence of select triorganophosphorus ligands, the hydroformylation of olefins with hydrogen and carbon monoxide. The variables include (1) the rhodium complex catalyst, (2) the olefin feed, (3) the triorganophosphorus ligand and its concentration, (4) a relatively low temperature range, (5) a relatively low total hydrogen and carbon monoxide pressure, and (6) a limitation on the partial pressure exerted by carbon monoxide. Embodiments of the present invention, while utilizing the basics of the hydroformylation processes described in U.S. Pat. No. 3,527,809, provide significant advances in such hydroformylation process technology.

Among the catalysts described in the '809 patent are compounds containing rhodium in complex combination with the carbon monoxide and triarylphosphorus ligands, in particular triarylphosphine ligands exemplified by triphenylphosphine (TPP). A typical active catalytic species is rhodium hydridocarbonyltris(triphenylphosphine) which has the formula $RhH(CO)(P(C_6H_5)_3)_3$. An excess of the triorganophosphorus ligand is used in such processes.

Other examples of active hydroformylation catalysts have been reported for phosphite and polyphosphite-based catalysts including those identified in U.S. Pat. Nos. 3,415,906, 4,567,302, 4,567,306, 4,599,206, 4,717,775, 4,835,299, 5,741,942, 5,741,944, and 6,090,987.

In typical hydroformlyation processes, a vaporizer (i.e., a distillation process) is used to separate the product from the catalyst solution. The product aldehydes are more volatile than the organophosphorous ligands such that, in general, the separation is relatively simple. However, despite the differences in boiling points between the aldehydes and the ligands, some traces of the organophosphorus ligand are still observed in the distilled product. This is discussed, for example, in U.S. Pat. No. 5,110,990 wherein organophosphorous ligands such as triphenylphosphine (TPP) have appreciable volatility at the vaporizer conditions, which typically involve elevated temperatures (>100° C.) and reduced pressure. Organophosphorous ligand in the aldehyde product stream can cause issues in downstream processes, especially hydrogenation as phosphorous ligands tend to be hydrogenation catalyst poisons. U.S. Pat. No. 5,110,990 also discusses the limitations on the overhead vapor stream from the vaporizer with respect to complex entrainment systems or sophisticated distillations systems that tend to promote heavies formation and higher pressure drops (requiring even more harsh vaporization conditions). The issues of heavies formation and high pressure drops are also recognized, for example, in U.S. Pat. No. 5,053,551, which teaches a reflux condenser and packing as part of the vaporizer that acts to condense and recycle higher boiler components. While the '551 patent focuses on aldehyde heavies, ligands would also be recycled to the vaporizer in this manner. However, the heavies are not removed via this scheme and the system would eventually choke on heavies (i.e., the heavies would eventually cause the system to fill with inerts). The packing and high counterflow would result in a significant pressure drop and higher heavies formation due to higher temperatures in the distillation.

U.S. Pat. No. 5,110,990 attempts to solve the problem described in the '551 patent by using a spray of crude aldehyde in the overhead of the vaporizer to condense the low volatility TPP without substantially reducing the amount of aldehyde heavies also being removed. However, this process returns the heavies back into the process fluid and can result in the system choking on heavies. Thus, the approach of U.S. Pat. No. 5,110,990 involves a balance of removing the aldehyde heavies from the catalyst solution with retaining the TPP. The net result is that the process used in U.S. Pat. No. 5,110,990 still leaves unacceptably high levels of phosphorous ligand (typically >20 ppm).

Following the vaporizer, redistillation of the crude aldehyde product to remove the contamination can be both costly and capital intensive. See, e.g., U.S. Pat. No. 4,792,636. U.S. Pat. No. 5,410,091 teaches using a second distillation system after the product/catalyst separation zone that leads to a batch still (a distillation system operating as a batch process, rather than continuous). Traces of organophosphorous ligand are also removed and the aldehyde can be recycled. This approach is similar to that described in U.S. Pat. No. 5,053,551, although the heavies are removed in the scheme of U.S. Pat. No. 5,410,091 because the bottoms stream is not sent directly back to the hydroformylation system. Nonetheless, this approach still suffers from complexity, pressure drop, and heavies formation issues.

Following hydroformylation, a pre-distillation step is common with vapor-phase hydrogenation processes to put the aldehydes into the vapor phase, but this can also remove organophosphorous ligand and heavies. Further, the process of reheating the aldehydes to distill at hydrogenation pressures results in additional heavies formation. However, with modern liquid phase hydrogenation processes wherein gasification prior to hydrogenation is not performed (see, e.g., U.S. Pat. No. 5,093,535 and U.S. Publication No. 2013/0316893), there is no means to remove this contamination and premature catalyst deactivation can occur because the contained organophosphorous ligand is present to deactivate the catalyst over time.

SUMMARY

The present invention advantageously provides simple and relatively inexpensive processes to reduce organophosphorous ligand contamination in an aldehyde product stream as part of a hydroformylation process without redistilling the entire aldehyde product stream prior to a hydrogenation step. Embodiments of the present invention can also advantageously facilitate the removal of aldehyde heavies from a hydroformylation system at their rate of formation so as to avoid buildup, while simultaneously controlling the level of organophosphorous ligand in the aldehyde product stream.

In one aspect, embodiments of the present invention provide a process for producing aldehydes wherein an olefinic compound, carbon monoxide, and hydrogen are reacted in the presence of a solubilized rhodium-phosphorous complex, the process comprising: (a) receiving a vaporized aldehyde product stream downstream from a hydroformylation reactor, the vaporized aldehyde product stream comprising aldehydes, phosphorous ligand, and aldehyde condensation by-products; (b) contacting the vaporized aldehyde product stream with a partial condenser so as to condense the phosphorous ligand and the by-products, wherein up to 10 weight percent of the vaporized stream is condensed; (c) removing the condensed phosphorous ligand and the condensed by-products from the liquid condensation stream using a refining column; and (d) further processing the vaporized aldehydes from the separate refining column.

In another aspect, embodiments of the present invention provide a process for producing aldehydes that comprises (a) reacting an olefinic compound, carbon monoxide, and hydrogen in the presence of a solubilized rhodium-phosphorous complex, free phosphorus ligand, and aldehyde condensation by-products to produce aldehydes in a liquid reaction solution; (b) vaporizing the liquid reaction solution to provide a vaporized aldehyde product stream comprising aldehydes, phosphorous ligand, and aldehyde condensation by-products; (c) partially condensing the vaporized product stream with a partial condenser to provide a liquid condensation stream comprising condensed phosphorous ligand and condensed by-products, and a gas stream comprising aldehydes, wherein up to 10 weight percent of the vaporized product stream is condensed; (d) removing the condensed phosphorous ligand and the condensed by-products from the liquid condensation stream using a refining column; and (e) further processing the vaporized aldehydes from the separate refining column.

These and other embodiments are described in more detail in the Detailed Description.

BRIEF DESCRIPTION OF THE DRAWINGS

FIG. 1 is a flow sheet illustrating a system for performing a process according to one embodiment of the present invention.

DETAILED DESCRIPTION

Processes of the present invention are implemented in the context of hydroformylation processes. In general, the inventive processes can be implemented in a wide variety of hydroformylation processes as known to those of skill in the art in view of the teachings herein. As is known to those of skill in the art, a hydroformylation process comprises contacting CO, $H_2$, and at least one olefin under hydroformylation conditions sufficient to form at least one aldehyde product in the presence of a catalyst comprising, as components, a transition metal and an organophosphorous ligand.

All references to the Periodic Table of the Elements and the various groups therein are to the version published in the CRC Handbook of Chemistry and Physics, 72nd Ed. (1991-1992) CRC Press, at page I-10.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety (or its equivalent US version is so incorporated by reference) especially with respect to the disclosure of definitions (to the extent not inconsistent with any definitions specifically provided in this disclosure) and general knowledge in the art.

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc. Also herein, the recitations of numerical ranges and/or numerical values, including such recitations in the claims, can be read to include the term "about." In such instances the term "about" refers to numerical ranges and/or numerical values that are substantially the same as those recited herein.

As used herein, the term "ppmw" means parts per million by weight.

For purposes of this invention, the term "hydrocarbon" is contemplated to include all permissible compounds having at least one hydrogen and one carbon atom. Such permissible compounds may also have one or more heteroatoms. In a broad aspect, the permissible hydrocarbons include acyclic (with or without heteroatoms) and cyclic, branched and unbranched, carbocyclic and heterocyclic, aromatic and nonaromatic organic compounds that can be substituted or unsubstituted.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxyalkyl, aminoalkyl, in which the number of carbons can range from 1 to 20 or more, preferably from 1 to 12, as well as hydroxy, halo, and amino. The permissible substituents can be one or more and the same or different for appropriate organic compounds. This invention is not intended to be limited in any manner by the permissible substituents of organic compounds.

As used herein, the term "hydroformylation" is contemplated to include, but not limited to, all permissible asymmetric and non-asymmetric hydroformylation processes that involve converting one or more substituted or unsubstituted olefinic compounds or a reaction mixture comprising one or more substituted or unsubstituted olefinic compounds to one or more substituted or unsubstituted aldehydes or a reaction mixture comprising one or more substituted or unsubstituted aldehydes.

The terms "reaction fluid," "reaction medium" and "catalyst solution" are used interchangeably herein, and may include, but are not limited to, a mixture comprising: (a) a metal-organophosphorous ligand complex catalyst, (b) free organophosphorous ligand, (c) aldehyde product formed in the reaction, (d) unreacted reactants, (e) a solvent for said metal-organophosphorous ligand complex catalyst and said free organophosphorous ligand, and, optionally, (f) one or more phosphorus acidic compounds formed in the reaction (which may be homogeneous or heterogeneous, and these compounds include those adhered to process equipment surfaces) and (g) organophosphorous ligand decomposition products such as the corresponding oxide. The reaction fluid can encompass, but is not limited to, (a) a fluid in a reaction zone, (b) a fluid stream on its way to a separation zone, (c) a fluid in a separation zone, (d) a recycle stream, (e) a fluid withdrawn from a reaction zone or separation zone, (f) a withdrawn fluid being treated with an aqueous buffer solution, (g) a treated fluid returned to a reaction zone or separation zone, (h) a fluid in an external cooler, and (i) ligand decomposition products and their salts.

"Upstream" means that a zone or step of a process is located or performed before that of a reference zone or step, e.g., the reaction zone of the hydroformylation process is located before or upstream of the vaporization zone which is located before or upstream of the gas-liquid separation zone.

"Downstream" means that a zone or step of a process is located or performed after that of a reference zone or step, e.g., the gas-liquid separation zone of the hydroformylation process is located after or downstream of the vaporization zone which is located after or downstream of the reaction zone.

Hydrogen and carbon monoxide may be obtained from any suitable source, including petroleum cracking and refinery operations. Syngas mixtures are a preferred source of hydrogen and CO.

Syngas (from synthesis gas) is the name given to a gas mixture that contains varying amounts of CO and $H_2$. Production methods are well known. Hydrogen and CO typically are the main components of syngas, but syngas may contain $CO_2$ and inert gases such as $N_2$ and Ar. The molar ratio of $H_2$ to CO varies greatly but generally ranges from 1:100 to 100:1 and preferably between 1:10 and 10:1. Syngas is commercially available and is often used as a fuel source or as an intermediate for the production of other chemicals. The most preferred $H_2$:CO molar ratio for chemical production is between 3:1 and 1:3 and usually is targeted to be between about 1:2 and 2:1 for most hydroformylation applications.

The substituted or unsubstituted olefinic unsaturated reactants that may be employed in the hydroformylation process include both optically active (prochiral and chiral) and non-optically active (achiral) olefinic unsaturated compounds containing from 2 to 40, preferably 3 to 20, carbon atoms. These compounds are described in detail in U.S. Pat. No. 7,863,487. Such olefinic unsaturated compounds can be terminally or internally unsaturated and be of straight-chain, branched chain or cyclic structures, as well as olefin mixtures, such as obtained from the oligomerization of propene, butene, isobutene, etc. (such as so called dimeric, trimeric or tetrameric propylene and the like, as disclosed, for example, in U.S. Pat. Nos. 4,518,809 and 4,528,403).

Prochiral and chiral olefins useful in the asymmetric hydroformylation that can be employed to produce enantiomeric aldehyde mixtures include those represented by the formula:

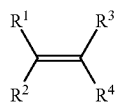

wherein $R^1$, $R^2$, $R^3$ and $R^4$ are the same or different (provided that $R^1$ is different from $R^2$ or $R^3$ is different from $R^4$) and are selected from hydrogen; alkyl; substituted alkyl, said substitution being selected from dialkylamino such as benzylamino and dibenzylamino, alkoxy such as methoxy and ethoxy, acyloxy such as acetoxy, halo, nitro, nitrile, thio, carbonyl, carboxamide, carboxaldehyde, carboxyl, and carboxylic ester; aryl including phenyl; substituted aryl including phenyl, said substitution being selected from alkyl, amino including alkylamino and dialkylamino such as benzylamino and dibenzylamino, hydroxy, alkoxy such as methoxy and ethoxy, acyloxy such as acetoxy, halo, nitrile, nitro, carboxyl, carboxaldehyde, carboxylic ester, carbonyl, and thio; acyloxy such as acetoxy; alkoxy such as methoxy and ethoxy; amino including alkylamino and dialkylamino such as benzylamino and dibenzylamino; acylamino and diacylamino such as acetylbenzylamino and diacetylamino; nitro; carbonyl; nitrile; carboxyl; carboxamide; carboxaldehyde; carboxylic ester; and alkylmercapto such as methylmercapto. It is understood that the prochiral and chiral olefins of this definition also include molecules of the above general formula where the R groups are connected to form ring compounds, e.g., 3-methyl-1-cyclohexene, and the like.

Illustrative optically active or prochiral olefinic compounds useful in asymmetric hydroformylation are described, for example, in U.S. Pat. Nos. 4,329,507, 5,360, 938 and 5,491,266.

A solvent advantageously is employed in the hydroformylation process. Any suitable solvent that does not unduly interfere with the hydroformylation process can be used. By way of illustration, suitable solvents for rhodium catalyzed hydroformylation processes include those disclosed, for example, in U.S. Pat. Nos. 3,527,809; 4,148,830; 5,312,996; and 5,929,289. Non-limiting examples of suitable solvents include saturated hydrocarbons (alkanes), aromatic hydrocarbons, water, ethers, aldehydes, ketones, nitriles, alcohols, esters, and aldehyde condensation products. Specific examples of solvents include: tetraglyme, pentanes, cyclohexane, heptanes, benzene, xylene, toluene, diethyl ether, tetrahydrofuran, butyraldehyde, and benzonitrile. The organic solvent may also contain dissolved water up to the saturation limit. Illustrative preferred solvents include ketones (e.g. acetone and methylethyl ketone), esters (e.g. ethyl acetate, di-2-ethylhexyl phthalate, 2,2,4-trimethyl-1,3-pentanediol monoisobutyrate), hydrocarbons (e.g. toluene), nitrohydrocarbons (e.g., nitrobenzene), ethers (e.g., tetrahydrofuran (THF)) and sulfolane. In rhodium catalyzed hydroformylation processes, it may be preferred to employ, as a primary solvent, aldehyde compounds corresponding to the aldehyde products desired to be produced and/or higher boiling aldehyde liquid condensation by-products, for example, as might be produced in situ during the hydroformylation process, as described for example in U.S. Pat. Nos. 4,148,830 and 4,247,486. The primary solvent will normally eventually comprise both aldehyde products and higher boiling aldehyde liquid condensation by-products ("heavies"), due to the nature of the continuous process. The amount of solvent is not especially critical and need only be sufficient to provide the reaction medium with the desired amount of transition metal concentration. Typically, the amount of solvent ranges from about 5 percent to about 95 percent by weight, based on the total weight of the reaction fluid. Mixtures of solvents may be employed.

Illustrative metal-organophosphorous ligand complexes employable in such hydroformylation reactions include metal-organophosphorous ligand complex catalysts. These catalysts, as well as methods for their preparation, are well known in the art and include those disclosed in the patents mentioned herein. In general, such catalysts may be preformed or formed in situ and comprise metal in complex combination with an organophosphorous ligand, carbon monoxide and optionally hydrogen. The ligand complex species may be present in mononuclear, dinuclear and/or higher nuclearity forms. However, the exact structure of the catalyst is not known.

The metal-organophosphorous ligand complex catalyst can be optically active or non-optically active. The metals can include Group 8, 9 and 10 metals selected from rhodium (Rh), cobalt (Co), iridium (Ir), ruthenium (Ru), iron (Fe), nickel (Ni), palladium (Pd), platinum (Pt), osmium (Os) and mixtures thereof, with the preferred metals being rhodium, cobalt, iridium and ruthenium, more preferably rhodium, cobalt and ruthenium, especially rhodium. Mixtures of these metals may be used. The permissible organophosphorous ligands that make up the metal-organophosphorous ligand complexes and free organophosphorous ligand include mono-, di-, tri- and higher polyorganophosphorus ligands. Mixtures of ligands may be employed in the metal-organophosphorous ligand complex catalyst and/or free ligand, and such mixtures may be the same or different.

The organophosphorous compounds that may serve as the ligand of the metal-organophosphorous ligand complex catalyst and/or free ligand may be of the achiral (optically inactive) or chiral (optically active) type and are well known in the art. Achiral organophosphorous ligands are preferred.

Organophosphine ligands are a preferred organophosphorous compound employable in the process of this disclosure and comprises any organic compound comprising one phosphorus atom covalently bonded to three alkyl, aryl or arylalkyl radicals, or combinations thereof. A mixture of organophosphine ligands may also be employed. Representative organomonophosphines include those having the formula:

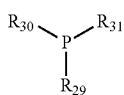

(I)

wherein each $R^{29}$, $R^{30}$ and $R^{31}$ may be the same or different and represent a substituted or unsubstituted alkyl radical containing from 1 to 30 carbon atoms or greater or an aryl radical containing from 4 to 40 carbon atoms or greater. Typical triarylphosphines may be found, and described in greater detail, in, for example, in U.S. Pat. No. 3,527,809, the disclosure of which is incorporated herein by reference. Illustrative organophosphine ligands are tributylphosphine, tricyclohexylphosphine, cyclohexyldiphenylphosphine, triphenylphosphine, trinaphthylphine, tritolylphosphine, tri(p-biphenyl)phosphine, tri(p-methoxyphenyl) phosphine, tri (m-chlorophenyl)-phosphine, p-N,N-dimethylaminophenyl bis-phenyl phosphine, and the like. Triphenyl phosphine, i.e. the compound of Formula II wherein each $R^{29}$, $R^{30}$ and $R^{31}$ is phenyl, is an example of a preferred organomonophosphine ligand. As pointed out previously, the reaction is effected in a liquid body containing excess, free triarylphosphine.

It is also known that during the hydroformylation process, triarylphosphines can generate alkyldiarylphosphines due to a degradation process described in U.S. Pat. No. 4,605,780. Thus, at least one or two of $R^{29}$, $R^{30}$ and $R^{31}$ may be derived from the olefin being used in the hydroformylation process.

These species tend to be more poisonous to catalysis activity than the parent triarylphosphine and often more volatile thus more of an issue for downstream hydrogenation catalysts and thus it is desirable to remove them from the product aldehyde.

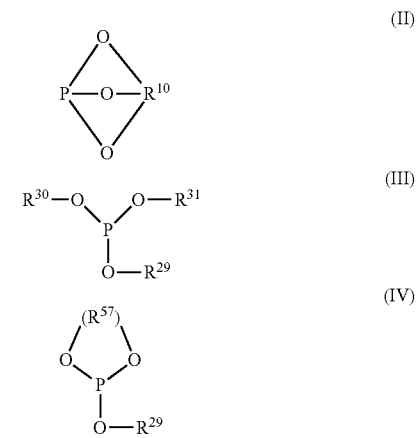

Phosphites such as shown in formulas (II), (III), and (IV) and phosphoramidites are also organophosphorous ligands that may be employed in this invention. $R^{10}$ represents a substituted or unsubstituted trivalent hydrocarbon radical containing from 4 to 40 carbon atoms or greater, such as trivalent acyclic and trivalent cyclic radicals, e.g., trivalent alkylene radicals such as those derived from 1,2,2-trimethylolpropane and the like, or trivalent cycloalkylene radicals such as those derived from 1,3,5-trihydroxycyclohexane and the like. Such monoorganophosphites may be found described in greater detail, for example, in U.S. Pat. No. 4,567,306. $R^{57}$ represents a divalent organic radical containing from 4 to 40 carbon atoms and may be alkyl, aryl, or substituted hydrocarbons. Examples of these diorganophosphites are described in U.S. Pat. Nos. 3,415,906 and 4,567, 302, 4,599,206, 4,717,775, 4,835,299, The preferred catalyst of this invention comprises rhodium complexed with carbon monoxide and a triarylphosphine ligand. The most desirable catalyst is free of metal-bound halogens such as chlorine, and contains hydrogen, carbon monoxide and triaryl phosphine complexed with rhodium metal to produce a catalyst soluble in the aforementioned liquid body and stable under the conditions of the reaction.

Rhodium is preferably introduced into the liquid body as a preformed catalyst, e.g., a stable crystalline solid, rhodium hydridocarbonyl-tris(triphenyl phosphine), RhH(CO) $(PPh_3)_3$. The rhodium can be introduced to the liquid body as a precursor form which is converted in situ into the catalyst. Examples of such precursor form are rhodium carbonyl triphenylphosphine acetylacetonate, $Rh_2O_3$, $Rh_4(CO)_{12}$, $Rh_6(CO)_{16}$, and rhodium dicarbonyl acetylacetonate. Both the catalyst compounds which will provide active species in the reaction medium and their preparation are known by the art, see Brown et al., Journal of the Chemical Society, 1970, pp. 2753-2764.

In ultimate terms the rhodium concentration in the liquid body can range from about 25 ppm to about 1200 ppm of rhodium calculated as free metal, and the triarylphosphine is present in the range of about 0.5 percent to about 30 percent by weight, based on the weight of the total reaction mixture, and in an amount sufficient to provide at least 10 moles of free triarylphosphine per mole of rhodium.

In general the optimum catalyst concentration depends on the concentration of the alpha-olefin, such as propylene. For example, the higher the propylene concentration the lower usually will be the catalyst concentration that can be used to achieve a given conversion rate to aldehyde products in a given size of reactor. Recognizing that partial pressures and concentration are related, the use of higher propylene partial pressure leads to an increased proportion of propylene in the "off gas" from the liquid body. Since it may be necessary to purge part of the gas stream from the product recovery zone before recycle to the liquid body in order to remove a portion of the propane which may be present, the higher the propylene content of the "off gas" is, the more propylene that will be lost in the propane purge stream. Thus it is necessary to balance the economic value of the propylene lost in the propane purge stream against the capital savings associated with lower catalyst concentration.

The metal-organophosphorous ligand complex catalysts may be in homogeneous or heterogeneous form. For instance, preformed rhodium hydrido-carbonyl-organophosphorous ligand catalysts may be prepared and introduced into a hydroformylation reaction mixture. More preferably, the rhodium-organophosphorous ligand complex catalysts can be derived from a rhodium catalyst precursor that may be introduced into the reaction medium for in situ formation of the active catalyst. For example, rhodium catalyst precursors such as rhodium dicarbonyl acetylacetonate, $Rh_2O_3$, $Rh_4(CO)_{12}$, $Rh_6(CO)_{16}$, $Rh(NO_3)_3$ and the like may be introduced into the reaction mixture along with the organophosphorous ligand for the in situ formation of the active catalyst. In a preferred embodiment, rhodium dicarbonyl acetylacetonate is employed as a rhodium precursor and reacted in the presence of a solvent with the organophosphorous ligand to form a catalytic rhodium-organophosphorous ligand complex precursor that is introduced into the reactor along with excess (free) organophosphorous ligand for the in situ formation of the active catalyst. In any event, it is sufficient that carbon monoxide, hydrogen and the organophosphorous ligand are all ligands that are capable of being complexed with the metal and that an active metal-organophosphorous ligand catalyst is present in the reaction mixture under the conditions used in the hydroformylation reaction. Carbonyl and organophosphorous ligands may be complexed to the rhodium either prior to or in situ during the hydroformylation process.

By way of illustration, a preferred catalyst precursor composition consists essentially of a solubilized rhodium carbonyl organophosphine ligand complex precursor, a solvent and, optionally, free organophosphine ligand. The preferred catalyst precursor composition can be prepared by forming a solution of rhodium dicarbonyl acetylacetonate, an organic solvent and a organophosphine ligand. The organophosphorous ligand readily replaces one of the carbonyl ligands of the rhodium acetylacetonate complex precursor as witnessed by the evolution of carbon monoxide gas.

Accordingly, the metal-organophosphorus ligand complex catalyst advantageously comprises the metal complexed with carbon monoxide and an organophosphorous ligand, said ligand being bonded (complexed) to the metal in a chelated and/or non-chelated fashion.

Mixtures of catalysts and ligands can be employed. The amount of metal-organophosphorous ligand complex catalyst present in the reaction fluid need only be that minimum amount necessary to provide the given metal concentration desired to be employed and that will furnish the basis for at least the catalytic amount of metal necessary to catalyze the particular hydroformylation process involved such as disclosed, for example, in the above-mentioned patents. In general, catalytic metal, e.g., rhodium, concentrations in the range of from 10 ppmw to 1000 ppmw, calculated as free metal in the reaction medium, should be sufficient for most processes, while it is generally preferred to employ from 10 to 500 ppmw of metal, and more preferably from 25 to 350 ppmw of metal.

In addition to the metal-organophosphorous ligand complex catalyst, free organophosphorous ligand (i.e., ligand that is not complexed with the metal) may also be present in the reaction medium. The significance of free ligand is taught in U.S. Pat. No. 3,527,809, GB 1,338,225, and Brown et al., supra., pages 2759 and 2761. The free organophosphorous ligand may correspond to any of the above-defined organophosphorous ligands discussed above. It is preferred that the free organophosphorous ligand be the same as the organophosphorous ligand of the metal-organophosphorous ligand complex catalyst employed. However, such ligands need not be the same in any given process. The hydroformylation process of this invention may involve from 0.1 moles or less to 100 moles or higher of free organophosphorous ligand per mole of metal in the reaction medium. Preferably, the hydroformylation process is carried out in the presence of from 1 to 80 moles of organophosphorous ligand per mole of metal present in the reaction medium. More preferably, for triarylphosphines, from 3 to 70 moles of triarylphosphine ligand are employed per mole of metal. Said amounts of organophosphorous ligand are the sum of both the amount of organophosphorous ligand that is bound (complexed) to the metal present and the amount of free organophosphorous ligand present. If desired, additional organophosphorous ligand can be supplied to the reaction medium of the hydroformylation process at any time and in any suitable manner, e.g. to maintain a predetermined level of free ligand in the reaction medium.

A slow loss in hydroformylation catalyst activity has been observed when phosphine ligand promoted metal catalysts are employed in processes that involve harsh conditions such as recovery of the aldehyde via a vaporizer-separator. It has been surprisingly found that an organic nitrogen compound when added to the hydroformylation reaction fluid, reduces the loss of catalyst activity.

Without wishing to be bound to any exact theory or mechanistic discourse it is believed that the encountered slow loss in catalytic activity of triarylphosphine-promoted metal hydroformylation catalysts is due at least in part to the harsh conditions such as employed in the separation and recovery of the aldehyde product from its reaction product fluid. For instance it has been found that when a triarylphosphine-promoted rhodium catalyst is placed under harsh conditions such as high temperature and low carbon monoxide partial pressure such as occur in a vaporizer, that the catalyst deactivates at an accelerated pace with time, due most likely to the formation of an inactive or less active rhodium species, which may also be susceptible to precipitation under prolonged exposure to such conditions. Such evidence is also consistent with the view that the active catalyst which under hydroformylation conditions is believed to comprise a complex of rhodium, triarylphosphine, carbon monoxide and hydrogen, losses at least some of its coordinated carbon monoxide ligand during harsh conditions such as exist during separation, e.g., vaporization, which provides a route for the formation of such catalytically inactive or less active rhodium species as discussed above. The means for preventing or minimizing such catalyst deactivation and/or precipitation comprises carrying out the portion of the hydroformylation process that involves harsh conditions such as the separation, e.g., vaporization, procedure of the hydroformylation process in the presence of one or more free heterocyclic nitrogen compounds as disclosed in WO2014149915, the disclosure of which is incorporated herein by reference.

Illustrative specific examples include imidazole and substituted imidazoles, such as 1-methylimidazole, 1-ethylimidazole, 1-n-propylimidazole, 1-isopropylimidazole, 1-butylimidazole, 2-methylimidazole, 2-ethylimidazole, 2-n-propylimidazole, 2-isopropylimidazole, 2-n-butylimidazole, 2-n-hexylimidazole, 2-n-heptylimidazole, and the like.

Benzimidazoles are especially preferred and illustrative specific examples of include benzimidazole and substituted benzimidazoles, such as 1-methylbenzimidazole, 1-ethylbenzimidazole, 1-n-propylbenzimidazole, 1-isopropylbenzimidazole, 1-butylbenzimidazole, 1-benzylbenzimidazole, 2-benzylbenzimidazole, 2-methylbenzimidazole, 2-ethylbenzimidazole, and the like. The most preferred heterocyclic nitrogen compound of all is benzimidazole.

The use of these optional amines also presents the problem of preventing them from being present in the resulting aldehyde product. Another advantage of some embodiments of the present invention is the reduction of these components by the same mechanism as for the organophosphorous ligand.

The hydroformylation process, and conditions for its operation, are well known. The hydroformylation processes may be asymmetric or non-asymmetric, the preferred processes being non-asymmetric, and may be conducted in any batch, continuous or semi-continuous fashion and may involve any catalyst liquid and/or gas recycle operation desired.

Thus, it should be clear that the particular hydroformylation process for producing such aldehydes from an olefinic unsaturated compound, as well as the reaction conditions and ingredients of the hydroformylation process are not critical features of this invention.

The liquid recycle procedure generally involves withdrawing a portion of the liquid reaction medium containing the catalyst and aldehyde product from the hydroformylation reactor, i.e., reaction zone, either continuously or intermittently, and recovering the aldehyde product therefrom by the conventional and preferred method of distilling it, i.e. vaporization separation, in one or more stages under normal, reduced or elevated pressure, as appropriate, in a separate distillation zone, the non-volatilized metal catalyst containing residue being recycled to the reaction zone as disclosed, for example, in U.S. Pat. No. 5,288,918. Condensation of the volatilized materials, and separation and further recovery thereof, e.g., by further distillation, can be carried out in any conventional manner, the crude aldehyde product can be passed on for further purification and isomer separation, if desired, and any recovered reactants, e.g., olefinic starting material and syngas, can be recycled in any desired manner to the hydroformylation zone (reactor). The recovered metal catalyst containing raffinate of such membrane separation or recovered non-volatilized metal catalyst containing residue of such vaporization separation can be recycled, to the hydroformylation zone (reactor) in any conventional manner desired.

In a gas recycle process such as described in U.S. Pat. No. 4,247,486, the reaction zone and vaporization zone are combined in that a large flow of gas is used to strip the product from the hydroformylation reaction. The volatiled stream is then condensed to recover the product and the noncondensed gases are recycled (typically with a compressor) to the reactor as the stripping gas. Such a large stripping gas flow also volatilizes the heavies but can also volatilize the organophosphorous ligands. Some embodiments of the present invention can also advantageously reduce the amount of these organophosphorous ligands that are present in the resulting product.

In a preferred embodiment, the hydroformylation reaction fluid includes any fluid derived from any corresponding hydroformylation process that contains at least some amount of four different main ingredients or components, i.e., the aldehyde product, a metal-organophosphorous ligand complex catalyst, free organophosphorous ligand and a solvent for said catalyst and said free ligand. The hydroformylation reaction mixture compositions can and normally will contain additional ingredients such as those that have either been deliberately employed in the hydroformylation process or formed in situ during said process. Examples of such additional ingredients include unreacted olefin starting material, carbon monoxide and hydrogen gases, and in situ formed by-products, such as saturated hydrocarbons and/or unreacted isomerized olefins corresponding to the olefin starting materials, ligand degradation compounds, and high boiling liquid aldehyde condensation by-products, as well as other inert co-solvent type materials or hydrocarbon additives, if employed.

The reaction conditions of the hydroformylation process may include any suitable type hydroformylation conditions heretofore employed for producing optically active and/or non-optically active aldehydes. The hydroformylation reaction conditions employed will be governed by the type of aldehyde product desired. For instance, the total gas pressure of hydrogen, carbon monoxide and olefin starting compound of the hydroformylation process may range from 1 to 69,000 kPa. In general, however, it is preferred that the process be operated at a total gas pressure of hydrogen, carbon monoxide and olefin starting compound of less than 14,000 kPa and more preferably less than 3,400 kPa. The minimum total pressure is limited predominantly by the amount of reactants necessary to obtain a desired rate of reaction. More specifically, the carbon monoxide partial pressure of the hydroformylation process is preferably from 1 to 6,900 kPa, and more preferably from 21 to 5,500 kPa, while the hydrogen partial pressure is preferably from 34 to 3,400 kPa and more preferably from 69 to 2,100 kPa. In general, the molar ratio of gaseous $H_2:CO$ may range from 1:10 to 100:1 or higher, the more preferred molar ratio being from 1:10 to 10:1. In general, the hydroformylation process may be conducted at any operable reaction temperature. Advantageously, the hydroformylation process is conducted at a reaction temperature from −25° C. to 200° C., preferably from 50° C. to 120° C.

The hydroformylation process may be carried out using one or more suitable reactors such as, for example, a fixed bed reactor, a fluid bed reactor, a continuous stirred tank reactor (CSTR) or a slurry reactor. The optimum size and shape of the catalysts will depend on the type of reactor used. The reaction zone employed may be a single vessel or may comprise two or more discrete vessels. The separation zone employed may be a single vessel or may comprise two or more discrete vessels. The reaction zone(s) and separation zone(s) employed herein may exist in the same vessel or in different vessels. For example, reactive separation techniques such as reactive distillation, and reactive membrane separation may occur in the reaction zone(s).

The hydroformylation process can be conducted with recycle of unconsumed starting materials if desired. The reaction can be conducted in a single reaction zone or in a plurality of reaction zones, and in series or in parallel. The reaction steps may be effected by the incremental addition of one of the starting materials to the other. Also, the reaction steps can be combined by the joint addition of the starting materials. When complete conversion is not desired or not obtainable, the starting materials can be separated from the product, for example by distillation, and the starting materials then recycled back into the reaction zone.

The hydroformylation process may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

The hydroformylation process of this invention may be conducted in one or more steps or stages. The exact number of reaction steps or stages will be governed by the best compromise between capital costs and achieving high catalyst selectivity, activity, lifetime and ease of operability, as well as the intrinsic reactivity of the starting materials in question and the stability of the starting materials and the desired reaction product to the reaction conditions.

In one embodiment, the hydroformylation process useful in this invention may be carried out in a multistaged reactor such as described, for example, in U.S. Pat. No. 5,728,893. Such multistaged reactors can be designed with internal, physical barriers that create more than one theoretical reactive stage per vessel.

It is generally preferred to carry out the hydroformylation process in a continuous manner. Continuous hydroformylation processes are well known in the art. The continuous process can be carried out in a single pass mode, i.e., wherein a vaporous mixture comprising unreacted olefinic starting material(s) and vaporized aldehyde product is removed from the liquid reaction mixture from whence the aldehyde product is recovered and make-up olefinic starting material(s), carbon monoxide and hydrogen are supplied to the liquid reaction medium for the next single pass through without recycling the unreacted olefinic starting material(s). Such types of recycle procedure are well known in the art and may involve the liquid recycling of the metal-organophosphorous complex catalyst fluid separated from the desired aldehyde reaction product(s), such as disclosed, for example, in U.S. Pat. No. 4,148,830 or a gas recycle procedure such as disclosed, for example, in U.S. Pat. No. 4,247,486, as well as a combination of both a liquid and gas recycle procedure if desired. The most preferred hydroformylation process comprises a continuous liquid catalyst recycle process. Suitable liquid catalyst recycle procedures are disclosed, for example, in U.S. Pat. Nos. 4,668,651; 4,774,361; 5,102,505 and 5,110,990.

As indicated above, desired aldehydes may be recovered from the reaction mixtures. For example, the recovery techniques disclosed in U.S. Pat. Nos. 4,148,830 and 4,247,486 can be used. For instance, in a continuous liquid catalyst recycle process the portion of the liquid reaction mixture (containing aldehyde product, catalyst, etc.), i.e., reaction fluid, removed from the reaction zone can be passed to a catalyst-product separation zone, e.g., vaporizer/separator, wherein the desired aldehyde product can be separated via distillation, in one or more stages, under normal, reduced or elevated pressure, from the liquid reaction fluid, condensed and collected in a product receiver, and further purified if desired. The remaining non-volatilized catalyst containing liquid reaction mixture may then be recycled back to the reactor as may if desired any other volatile materials, e.g., unreacted olefin, together with any hydrogen and carbon monoxide dissolved in the liquid reaction after separation thereof from the condensed aldehyde product, e.g., by distillation in any conventional manner. In general, it is preferred to separate the desired aldehydes from the catalyst-containing reaction mixture under reduced pressure and at low temperatures so as to avoid possible degradation of the organophosphorous ligand and reaction products.

More particularly, distillation and separation of the desired aldehyde product from the metal-organophosphorous complex catalyst containing reaction fluid may take place at any suitable temperature desired. In general, it is preferred that such distillation take place at relatively low temperatures, such as below 150° C., and more preferably at a temperature in the range of from 50° C. to 140° C. It is also generally preferred that such aldehyde distillation take place under reduced pressure, e.g., a total gas pressure that is substantially lower than the total gas pressure employed during hydroformylation when low boiling aldehydes (e.g., $C_3$ to $C_5$) are involved or under vacuum when high boiling aldehydes (e.g. $C_7$ or greater) are involved. For instance, a common practice is to subject the liquid reaction product medium removed from the hydroformylation reactor to a pressure reduction so as to volatilize a substantial portion of the unreacted gases dissolved in the liquid medium that now contains a much lower synthesis gas concentration than is present in the reaction medium to the distillation zone, e.g. vaporizer/separator, wherein the desired aldehyde product is distilled. In general, distillation pressures ranging from vacuum pressures on up to total gas pressure of 340 kPa should be sufficient for most purposes.

Alternatively, recycle gas can be used in a stripping gas vaporizer as described in PCT Publication No. WO2010/003073.

Embodiments of the present invention improve conventional hydroformylation processes. Embodiments of the present invention generally involve a partial condensation of the vaporized product prior to subsequent processing as described further herein.

In one embodiment of the present invention, in a process for producing aldehydes wherein an olefinic compound, carbon monoxide, and hydrogen are reacted in the presence of a solubilized rhodium-phosphorous complex, the process comprises (a) receiving a vaporized aldehyde product stream downstream from a hydroformylation reactor, the vaporized aldehyde product stream comprising aldehydes, phosphorous ligand, and aldehyde condensation by-products; (b) contacting the vaporized aldehyde product stream with a partial condenser so as to condense the phosphorous ligand and the by-products, wherein up to 10 weight percent of the vaporized stream is condensed; (c) removing the condensed phosphorous ligand and the condensed by-products from the liquid condensation stream using a refining column; and (d) further processing the vaporized aldehydes from the separate refining column. In some embodiments, the uncondensed aldehyde product stream from step (b) is transported for further processing.

In another embodiment, a process for producing aldehydes of the present invention comprises (a) reacting an olefinic compound, carbon monoxide, and hydrogen in the presence of a solubilized rhodium-phosphorous complex, free phosphorus ligand, and aldehyde condensation by-products to produce aldehydes in a liquid reaction solution; (b) vaporizing the liquid reaction solution to provide a vaporized aldehyde product stream comprising aldehydes, phosphorous ligand, and aldehyde condensation by-products; (c) partially condensing the vaporized product stream with a partial condenser to provide a liquid condensation stream comprising condensed phosphorous ligand and condensed by-products, and a gas stream comprising aldehydes, wherein up to 10 weight percent of the vaporized product stream is condensed; (d) removing the condensed phosphorous ligand and the condensed by-products from the liquid condensation stream using a refining column; and (e) further processing the vaporized aldehydes from the separate refining column.

In some embodiments, the aldehyde condensation by-products have a boiling point at least 30° C. greater than the boiling point of the aldehydes.

In some embodiments, up to 5 weight percent of the vaporized product stream is condensed in the partial condenser. Up to 4 weight percent of the vaporized product stream is condensed in the partial condenser in some embodiments.

In some embodiments, the condensed phosphorus ligand and the condensed by-products are not returned to the process.

In some embodiments, the olefinic compound is an olefin having from 2 to 8 carbon atoms.

In some embodiments, the phosphorus ligand is a triorganophosphine compound. The phosphorus ligand comprises triphenylphosphine in some embodiments. The phosphorus ligand, in some embodiments, comprises cyclohexyldiphenylphosphine.

In some embodiments, the vaporized aldehyde product stream further comprises amines, and wherein the liquid condensation stream from the partial condenser further comprises condensed amines.

FIG. 1 illustrates a system that can be used for carrying out a process according to an embodiment of the present invention.

As shown in FIG. 1, the vaporized product stream (3b) leaving a vaporizer (2) and optional demister (4), as described above, is introduced to a partial condenser (5) where only a small portion of the vapor is condensed. The vaporized product stream is preferably the vaporized product from a catalyst-product separation zone (e.g., a vaporizer (2)) but can also include streams from knockout pot vents, pressure control vents, high and low pressure vaporizer vents, and/or aldehyde refining vents. The condensed material (7) is then refined in refining column (8) to recover any aldehyde product and remove the organophosphorous ligand and heavies via line (10) without returning the heavies to the hydroformylation process (in contrast to U.S. Pat. No. 5,110,990). The remaining vapor in stream (6) proceeds to further processing (e.g., condensation to liquid or being fed to a distillation system).

Focusing on the entire flow sheet shown in FIG. 1, a catalyst solution (1) comprising catalyst and aldehyde product (aldehydes) from a hydroformylation reactor are introduced to the vaporizer (2) wherein the crude aldehyde product and other volatiles leave via stream (3) past an optional demister (4) towards the partial condenser (5). At the partial condenser (5), most of the vaporized product continues for further processing via line (6) but a small stream of condensed material leaves via line (7) to a refining column (8) wherein additional aldehydes are recovered via line (9), and heavies (e.g., aldehyde condensation by-products, amines (if present)) and organophosphorous ligand leaves via line (10). The non-volatilized material from the vaporizer (2) exits the bottom via line (11) and is sent back to the hydroformylation reactor system, or other catalyst solution processing, before returning to the reactors. Optionally, stream (12) is introduced as a crude aldehyde spray system to the vaporizer overhead as described in U.S. Pat. No. 5,110,990. Stream (9) can be returned to the vapor stream either before or after the partial condenser (5), or sent separately for further processing (e.g., an isomer separation column).

Only a small portion of the stream (3) flow is condensed in the partial condenser (5). The mass ratio of stream (7) to the sum of streams (6) and (7) should be no greater than 10 wt %, preferably less than 5 wt % and most preferably less than 4 wt %. Since only a small portion of the total product flow is diverted, the size of the refining column (8) is considerably reduced compared to redistilling the entire product flow, such that embodiments of the present invention can provide significant capital and steam savings.

The partial condenser (5) can be any appropriate heat exchange device and its design is not critical to the invention, as long as the partially condensed process stream exiting the cooler is treated so that the liquid and gas phases of the stream are in thermodynamic equilibrium with each other and have been cooled sufficiently to create a liquid stream of the desired flow. For instance, the heat exchange device could consist of a plurality of tubes within a shell where the process stream flows through the shell and a cooling medium such as cooling water or some other cool fluid passes through the tubes. Alternatively, the process could pass through the tubes and the cooling medium could pass through the shell. Alternatively, the heat exchange device could be of any design well-known in the art that achieves the preferred performance. The size of the exchanger, the specific design of the shell and the tubes, their arrangement relative to each other, their orientation, and flow paths through the shell and tube, are not critical to the invention and can be any design that is well-known in the art and achieves the degree of partial condensation required. It is preferable for the amount of cooling to be controlled so that the amount of partial condensation can be controlled. This can be accomplished by varying the temperature and/or the flow of the cooling medium that flows through the exchanger. It is preferable that the process stream experiences very little resistance to its flow in the exchanger, so that the exit pressure of the partially-condensed process fluid is very close to its inlet pressure; a pressure drop of less than 27 kPa, preferably less than 14 kPa is preferred, but again is not critical to the invention.

The heat exchange device or partial condenser should be followed by a process step whereby the partially condensed liquid is separated from the remaining vapor. This step could be a simple vessel as is well-known in the art, and this vessel could be connected to, or separate from, the heat exchange device. The gas-liquid separation should be sufficient so that the desired degree of removal is obtained from the gaseous phase. The design of the separation vessel is not critical to the invention and can be any such vessel well-known in the art. For instance, in FIG. 1, partial condenser (5) is depicted as encompassing a heat exchange device and a gas/liquid separation step in one vessel.

The operation of column (8) to distill aldehyde from the heavies and organophosphorous ligand is similar to those described for the operation of the catalyst-product separation zone above but can be more vigorous since there should be no catalyst present to be deactivated, and any ligand decomposition products will be removed with the heavies purge. Generally speaking, these conditions are well known in the art and should not involve excessively high distillation temperatures to minimize aldehyde heavies formation. Since only a small portion of the total product flow is involved, the total amount of heavies formation is much reduced compared to prior art designs which involve distillation of substantially all of the aldehyde output (i.e., the ratio of stream (3) condensed to the equivalent of stream (7) is essentially 100 wt % in prior art designs in contrast to no greater than 10% in the present invention). In a preferred embodiment, the pressure in the refining column (8) is as low as possible to minimize column base temperature, while being high enough that the vapor effluent from the top of the column can be directly fed back to the partial condenser (5) without requiring compression, pumping, etc.

Stream (10) can be further processed and the organophosphorous ligand(s) can be separated and recycled from the aldehyde heavies in a separate distillation system, for example, if desired. Line (13) is the return line from the demister (4) which may be integral to the vaporizer rather than a separate unit.

Illustrative non-optically active aldehyde products that can be made using embodiments of the present invention include e.g., propionaldehyde, n-butyraldehyde, isobutyraldehyde, n-valeraldehyde, 2-methyl 1-butyraldehyde, 3-methyl 1-butyraldehyde, hexanal, hydroxyhexanal, 2-methyl 1-heptanal, nonanal, 2-methyl-1-octanal, decanal, adipaldehyde, 2-methylglutaraldehyde, 2-methyladipaldehyde, 3-hydroxypropionaldehyde, 6-hydroxyhexanal, alkenals, e.g., 2-, 3- and 4-pentenal, alkyl 5-formylvalerate, 2-methyl-1-nonanal, 2-methyl 1-decanal, 3-propyl-1-undecanal, pentadecanal, 3-propyl-1-hexadecanal, eicosanal, 2-methyl-1-tricosanal, pentacosanal, 2-methyl-1-tetracosanal, nonacosanal, 2-methyl-1-octacosanal, hentriacontanal, and 2-methyl-1-triacontanal.

Illustrative optically active aldehyde products that can be made using embodiments of the present invention include (enantiomeric) aldehyde compounds such as, e.g. S-2-(p-isobutylphenyl)-propionaldehyde, S-2-(6-methoxy-2-naphthyl)propionaldehyde, S-2-(3-benzoylphenyl)-propionaldehyde, S-2-(3-fluoro-4-phenyl)phenylpropionaldehyde, and S-2-(2-methylacetaldehyde)-5-benzoylthiophene.

All parts and percentages in the following examples are by weight unless otherwise indicated. Pressures are given as absolute pressure unless otherwise indicated. The organophosphorous ligands and aldehyde heavies in the product streams are measured by gas chromatography and/or gas chromatography coupled with mass spectroscopy.

Some embodiments of the invention will now be described in detail in the following Example.

Example

The process is essentially the same as the conventional Oxo reaction system with two identical CSTR reactors depicted in Fig. 4.6 of Process Economics Program Report 21D, OXO ALCOHOLS (December 1999), available from IHS Inc. The catalyst is a typical Rh-TPP catalyst as described in Example 13 of U.S. Pat. No. 4,148,830, and the reaction conditions are essentially those of Example 13 for propylene except that the initial target rhodium concentration for the first reactor is 250-300 ppm Rh. The catalyst system is a typical Rh-TPP catalyst operating as described in U.S. Pat. No. 4,605,780 and PCT Publication No. WO2014/149915, and typically comprises 10-12 wt % TPP in the reaction fluid with up to a steady-state concentration of 3% propyldiphenylphosphine (PDPP).

To assist in explanation of this example, reference numbers to equipment/streams in FIG. 1 are used to identify corresponding equipment/streams described in this Example.

Selected process conditions and the rate of unrefined aldehyde production are shown in Table 1 based on a olefin feed rate of 32,200 kg/hr of propylene (90-95% purity):

TABLE 1

|  | Temperature (° C.) | Pressure (mPa) |
| --- | --- | --- |
| LP Vaporizer Catchpot (2) | 142 (gas) 111 (Liquid) | 0.203 |
| Partial condenser (5) | 85 | 0.193 |
| TPP stripping column (8) | 92 (top) 112 (bottom) | 0.196 |

A portion of the liquid reaction solution is continuously pumped from Reactor 2 to a series of 2 vaporizers, the first at high pressure to vent uncondensible gases (e.g., syngas, argon, nitrogen) then a second lower temperature vaporizer to remove aldehyde product. The effluent stream from the second vaporizer is sent to a gas-liquid separator located at the bottom of the vaporizer, where vaporized aldehyde product is separated from the non-volatile components of the liquid reaction solution. The vaporized aldehyde product stream is sent through a demister (4) and then a partial condenser (5), where a portion is condensed and sent to the TPP refining column (8); the remaining vaporized aldehyde is condensed and collected in a product receiver.

The non-volatile components, including catalyst to be recycled, from the gas-liquid separator (2) is pumped through a recycle line (11) into Reactor 1 (not shown). The flow of stream (12) is 540 kg/hr. Stream (9) is returned to the process before the partial condenser (5).

The conditions in the partial condenser (5) and TPP stripping column (8) are given in Table 1 based on a process feeding 51,000 kg/hr of catalyst-product solution (corresponding to stream (1) in FIG. 1) to the second vaporizer catchpot (corresponding to (2) in FIG. 1). The conditions in condenser (5) are such that stream (7) flow rate is 1,100 kg/hr (3.4% of the vaporized stream). The organophosphorous ligand level in the resulting stream (6) is typically less than 10 ppm and the heavies are less than 10 ppm. Without the invention (bypassing the partial condenser), the TPP concentration in the crude product would be greater than 100 ppm, propyldiphenylphosphine (PDPP) greater than 150 ppm, and heavies above 2000 ppm. The heavies purge stream (10) is composed of 2.6% TPP, 4.5% PDPP, and 50% heavies. The stream (10) flow rate is 130 kg/hr or 0.4 wt % of the feed stream (1) thus represents a very small process loss and effectively removes the heavies formed in the reaction system as well as the volatilized TPP. Stream (10) comprises 50% heavies, 3% TPP and 4% CHDPP.

What is claimed is:

1. A process for producing aldehydes wherein an olefinic compound, carbon monoxide, and hydrogen are reacted in the presence of a solubilized rhodium-phosphorous complex, the process comprising:

(a) receiving a vaporized aldehyde product stream downstream from a hydroformylation reactor, the vaporized aldehyde product stream comprising aldehydes, phosphorous ligand, and aldehyde condensation by-products;

(b) contacting the vaporized aldehyde product stream with a partial condenser so as to condense the phosphorous ligand and the by-products, wherein up to 10 weight percent of the vaporized stream is condensed and wherein the partial condenser comprises a heat exchange device;
(c) removing the condensed phosphorous ligand and the condensed by-products from the liquid condensation stream using a refining column; and
(d) further processing the vaporized aldehydes from the separate refining column.

2. The process of claim 1, wherein the uncondensed aldehyde product stream from step (b) is transported for further processing.

3. A process for producing aldehydes, the process comprising:
(a) reacting an olefinic compound, carbon monoxide, and hydrogen in the presence of a solubilized rhodium-phosphorous complex, free phosphorus ligand, and aldehyde condensation by-products to produce aldehydes in a liquid reaction solution;
(b) vaporizing the liquid reaction solution to provide a vaporized aldehyde product stream comprising aldehydes, phosphorous ligand, and aldehyde condensation by-products;
(c) partially condensing the vaporized product stream with a partial condenser to provide a liquid condensation stream comprising condensed phosphorous ligand and condensed by-products, and a gas stream comprising aldehydes, wherein up to 10 weight percent of the vaporized product stream is condensed and wherein the partial condenser comprises a heat exchange device;
(d) removing the condensed phosphorous ligand and the condensed by-products from the liquid condensation stream using a refining column; and
(e) further processing the vaporized aldehydes from the separate refining column.

4. The process according to claim 1, wherein the aldehyde condensation by-products have a boiling point at least 30° C. greater than the boiling point of the aldehydes.

5. The process according to claim 1, wherein the olefinic compound is an olefin having from 2 to 8 carbon atoms.

6. The process according to claim 1, wherein up to 5 weight percent of the vaporized product stream is condensed.

7. The process according to claim 1, wherein up to 4 weight percent of the vaporized product stream is condensed.

8. The process according to claim 1, wherein the phosphorus ligand is a triorganophosphine compound.

9. The process according to claim 1, wherein the phosphorus ligand comprises triphenylphosphine.

10. The process according to claim 1, wherein the phosphorus ligand comprises cyclohexyldiphenylphosphine.

11. The process according to claim 1, wherein the condensed phosphorus ligand and the condensed by-products are not returned to the process.

12. The process according to claim 1, wherein the vaporized aldehyde product stream further comprises amines, and wherein the liquid condensation stream from the partial condenser further comprises condensed amines.

\* \* \* \* \*